(12) United States Patent
Debrus et al.

(10) Patent No.: US 7,758,866 B2
(45) Date of Patent: Jul. 20, 2010

(54) VACCINE AGAINST HPV16 AND HPV18 AND AT LEAST ANOTHER HPV TYPE SELECTED FROM HPV 31, 45 OR 52

(75) Inventors: Serge Debrus, Rixensart (BE); Marie-Therese Martin, Rixensart (BE); Robert John Stephen, Brentford (GB); Jean Stephenne, Rixensart (BE); Martine Anne Cecile Wettendorff, Rixensart (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 348 days.

(21) Appl. No.: 11/570,603

(22) PCT Filed: Jun. 14, 2005

(86) PCT No.: PCT/EP2005/006461

§ 371 (c)(1),
(2), (4) Date: Dec. 14, 2006

(87) PCT Pub. No.: WO2005/123125

PCT Pub. Date: Dec. 29, 2005

(65) Prior Publication Data

US 2008/0014220 A1 Jan. 17, 2008

Related U.S. Application Data

(63) Continuation-in-part of application No. 11/114,301, filed on Apr. 26, 2005, now abandoned.

(30) Foreign Application Priority Data

Jun. 16, 2004 (GB) .................................. 0413510.9

(51) Int. Cl.
A61K 39/12 (2006.01)
(52) U.S. Cl. .................................................. 424/204.1
(58) Field of Classification Search ....................... None
See application file for complete search history.

(56) References Cited

U.S. PATENT DOCUMENTS

| 5,855,891 | A | 1/1999 | Lowy et al. |
| 6,251,678 | B1 | 6/2001 | Volkin et al. |
| 6,908,613 | B2 | 6/2005 | Wilson et al. |
| 6,936,255 | B1 | 8/2005 | Wettendorff |
| 7,101,560 | B2 | 9/2006 | Wettendorff |
| 7,217,419 | B2 * | 5/2007 | Wettendorff ............. 424/204.1 |
| 7,357,936 | B1 | 4/2008 | Garcon |
| 7,416,846 | B2 | 8/2008 | Wettendorff |
| 2005/0123562 | A1 | 6/2005 | Wettendorff |
| 2006/0251676 | A1 | 11/2006 | Dubin et al. |

FOREIGN PATENT DOCUMENTS

| EP | 689454 B1 | 1/1996 |
| EP | 1 410 805 | 4/2004 |
| WO | WO 96/11274 | 4/1996 |
| WO | WO 99/45957 | 9/1999 |
| WO | WO 99/50424 | 10/1999 |
| WO | WO 00/23105 | 4/2000 |
| WO | WO01/17551 | 3/2001 |
| WO | WO 01/97840 | 12/2001 |
| WO | WO 00/09699 | 2/2002 |
| WO | WO 03/077942 | * 9/2003 |
| WO | WO03/077942 | 9/2003 |
| WO | WO 95/17209 | 7/2004 |
| WO | WO 2004/056389 | 7/2004 |
| WO | WO2005/032586 | 4/2005 |

OTHER PUBLICATIONS

Villa et al ( Lancet Oncology 6:271-78, 2005).*
Munoz et al (International Journal of Cancer 111:278-285, 2004).*
Villa et al ("A dose-ranging safety and immunogenicity study of a quadrivalent HPV(type 6/11/16/18) L1 VLP vaccine in women", HPV Clinical Workshop & 20th International Papillomavirus Conference 2002, Oct. 4-9, 2002, Paris, Institute Pasteur) (no page number available).*
Villa et al ("A dose-ranging safety and immunogenicity study of a quadrivalent HPV(type 6/11/16/18) L1 VLP vaccine in women", HPV Clinical Workshop & 20th International Papillomavirus Conference 2002, Oct. 4-9, 2000, Paris, Institute Pasteur) (no page number available.*
Bachtiary, et al., Impact of multiple HPV infection on response to treatment and survival in pts. receiving radical radiotherapy for cervical cancer, *International Journal of Cancer, Journal International Du Cancer*, US, vol. 102, No. 3, pp. 237-243 (2002).
Bass, et al., Progress in the search of a vaccine against human papilloma virus, *IAVI Report* Oct./Nov. 2002, Online, Oct. 10, 2002, retrieved from the internet—www.aegis.com/pubs/iavi/2002/IAVI2002-1003.html, retrieved on Apr. 21, 2004.
Clifford, et al., "Human papillomavirus types in invasive cervical cancer worldwide: a meta-analysis", *British J. of Cancer*, vol. 88, p. 63-73 (2003).
Harro, et al., "Safety and immunogenicity trial in adult volunteers of a human papillomavirus 16 L1 virus-like particle vaccine", *J. of the National Cancer Institute*, vol. 93, No. 4, p. 284-292 (2001).
Koutsky, et al., "A controlled trial of a human papillomavirus type 16 vaccine", *N. Engl. J. Med.*, vol. 347, No. 21, p. 1645-1651 (2002).
Moore, et al., "Absence of canine oral papillomavirus DNA following prophylactic L1 particle-mediated immunotherapeutic delivery vaccination", *Journal of General Virology*, 83:2299-2301 (2002).
Munoz, et al., "Against Which Human Papillomavirus Types Shall We Vaccinate and Screen? The International Perspective", *Int. J. Cancer*, vol. 111, 278-285 (2004).

(Continued)

Primary Examiner—Mary E Mosher
(74) Attorney, Agent, or Firm—Gwynedd Warren; GlaxoSmithKline - Global Patents

(57) ABSTRACT

An immunogenic composition and methods for producing said composition, the composition comprising VLPs from HPV 16 and 18 and at least one other HPV cancer type, the other cancer type being selected from the list consisting of HPV types 31, 45 and 52, wherein the dose of the VLP of the at least one other cancer types is reduced relative to that of HPV 16 or 18.

21 Claims, No Drawings

OTHER PUBLICATIONS

Schiller, et al., "Papillomavirus-like particles and HPV vaccine development", *Seminars in Cancer Biology*, vol. 7, No. 6, pp. 373-382 (1996).

Schiller, et al, "Papillomavirus-like particle base vaccines: cervical cancer and beyond", *Expert Opinion on Biological Therapy*, Ashley, London, GB, vol. 1, No. 4, p. 571-581 (2001).

Suzich, et al., "Systemic immunization with papillomavirus L1 protein completely prevents the development of viral mucosal papillomas", *Proceedings of the National Academy of Sciences of USA, National Academy of Science*, vol. 92, p. 11553-11557 (1995).

Thompson, et al., "Immunogenicity & reactogenicity of a recombinant HPV6 fusion protein vaccine adjuvanted with monophosphoryl lipid A", *Biochemical Society Transactions*, vol. 274S p. 25 (1997).

Wheeler, "Preventive vaccines for cervical cancer" *Salud Publica de Mexico*, vol. 39 No. 4, pp. 283-287 (1997).

White, et al., "In Vitro Infection and Type-Restricted Antibody-Mediated Neutralization of Authentic Human Papillomavirus Type 16", *Journal of Virology*, vol. 72, No. 2, pp. 959-964 (1998).

Zhehbe, et al., "Human papillomavirus infection and invasive cervical neoplasia: A study of prevalence and morphology", *Journal of Pathology*, vol. 181, p. 270-274 (1997).

U.S. Appl. No. 11/367,601, filed Dec. 16, 2005, Dubin, et al.

U.S. Appl. No. 10/540,099, filed Jun. 29, 2006, Dubin, et al.

U.S. Appl. No. 11/477,879, filed Jun. 29, 2006, Sloaui, Moncef Mohammed.

Giroglou et al., "Immunological Analyses of Human Papillomavirus Capsids", Vaccine, Butterworth Scientific, vol. 19, No. 13-14, 2001, pp. 1783-1793.

GlaxoSmithKline HPV Vaccine Study Group, Harper et al., "Efficacy of a Bivalent L1 Virus-Like Particle Vaccine in Prevention of Infection with Human Papillomavirus Types 16 and 18 in Young Women: A Rand. Contr. Trial", The Lancent (Limited), vol. 364, No. 9447, Nov. 13, 2004, pp. 1757-1765.

Reinis, M., Technology Evaluation: HPV Vaccine (Quadrivalent), Aventis Pasteur, Current Opinion in Molecular Therapeutics, vol. 6, No. 2, Apr. 2004, pp. 206-211.

Roden et al., "Assessment of the Serological Relatedness of Genital Human Papillomaviruses by Hemagglutination Inhibition", J. of Virology, vol. 70, No. 5, May 1996, pp. 3298-3301.

Villa et al., "Prophylactic Quadrivalent Human Papillomavirus (Types 6, 11, 16 and 18) L1 Virus-Like Particle Vaccine in Prevention of Infection with Human Papillomavirus Types 16 and 18 in Young Women: A Rand. Controlled Trial", Lancent Oncology, vol. 6, No. 5, May 2005, pp. 271-278.

Billich A, "HPV Vaccine Medimmune/ GlaxoSmithKline", Current Opinion in Invest. Drugs, vol. 4, No. 2, Feb. 2003, pp. 210-213.

* cited by examiner

SEQUENCE LISTING

<160> NUMBER OF SEQ ID NOS: 2

<210> SEQ ID NO 1
<211> LENGTH: 471
<212> TYPE: PRT
<213> ORGANISM: Human Papillomavirus HPV 16

<400> SEQUENCE: 1

```
Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Ala Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Pro Gly Gly Thr Leu Glu Asp
```

```
                    405                 410                 415
Thr Tyr Arg Phe Val Thr Ser Gln Ala Ile Ala Cys Gln Lys His Thr
                420                 425                 430
Pro Pro Ala Pro Lys Glu Asp Pro Leu Lys Lys Tyr Thr Phe Trp Glu
            435                 440                 445
Val Asn Leu Lys Glu Lys Phe Ser Ala Asp Leu Asp Gln Phe Pro Leu
        450                 455                 460
Gly Arg Lys Phe Leu Leu Gln
465                 470

<210> SEQ ID NO 2
<211> LENGTH: 472
<212> TYPE: PRT
<213> ORGANISM: Human Papillomavirus HPV 18

<400> SEQUENCE: 2

Met Ala Leu Trp Arg Pro Ser Asp Asn Thr Val Tyr Leu Pro Pro Pro
  1               5                  10                  15
Ser Val Ala Arg Val Val Asn Thr Asp Asp Tyr Val Thr Arg Thr Ser
                 20                  25                  30
Ile Phe Tyr His Ala Gly Ser Ser Arg Leu Leu Thr Val Gly Asn Pro
             35                  40                  45
Tyr Phe Arg Val Pro Ala Gly Gly Asn Lys Gln Asp Ile Pro Lys
         50                  55                  60
Val Ser Ala Tyr Gln Tyr Arg Val Phe Arg Val Gln Leu Pro Asp Pro
 65                  70                  75                  80
Asn Lys Phe Gly Leu Pro Asp Asn Ser Ile Tyr Asn Pro Glu Thr Gln
                 85                  90                  95
Arg Leu Val Trp Ala Cys Val Gly Val Glu Ile Gly Arg Gly Gln Pro
                100                 105                 110
Leu Gly Val Gly Leu Ser Gly His Pro Phe Tyr Asn Lys Leu Asp Asp
            115                 120                 125
Thr Glu Ser Ser His Ala Ala Thr Ser Asn Val Ser Glu Asp Val Arg
        130                 135                 140
Asp Asn Val Ser Val Asp Tyr Lys Gln Thr Gln Leu Cys Ile Leu Gly
145                 150                 155                 160
Cys Ala Pro Ala Ile Gly Glu His Trp Ala Lys Gly Thr Ala Cys Lys
                165                 170                 175
Ser Arg Pro Leu Ser Gln Gly Asp Cys Pro Pro Leu Glu Leu Lys Asn
            180                 185                 190
Thr Val Leu Glu Asp Gly Asp Met Val Asp Thr Gly Tyr Gly Ala Met
        195                 200                 205
Asp Phe Ser Thr Leu Gln Asp Thr Lys Cys Glu Val Pro Leu Asp Ile
    210                 215                 220
Cys Gln Ser Ile Cys Lys Tyr Pro Asp Tyr Leu Gln Met Ser Ala Asp
225                 230                 235                 240
Pro Tyr Gly Asp Ser Met Phe Phe Cys Leu Arg Arg Glu Gln Leu Phe
                245                 250                 255
Ala Arg His Phe Trp Asn Arg Ala Gly Thr Met Gly Asp Thr Val Pro
            260                 265                 270
Pro Ser Leu Tyr Ile Lys Gly Thr Gly Met Arg Ala Ser Pro Gly Ser
        275                 280                 285
Cys Val Tyr Ser Pro Ser Pro Ser Gly Ser Ile Val Thr Ser Asp Ser
    290                 295                 300
```

-continued

```
Gln Leu Phe Asn Lys Pro Tyr Trp Leu His Lys Ala Gln Gly His Asn
305                 310                 315                 320

Asn Gly Val Cys Trp His Asn Gln Leu Phe Val Thr Val Val Asp Thr
                325                 330                 335

Thr Arg Ser Thr Asn Leu Thr Ile Cys Ala Ser Thr Gln Ser Pro Val
            340                 345                 350

Pro Gly Gln Tyr Asp Ala Thr Lys Phe Lys Gln Tyr Ser Arg His Val
        355                 360                 365

Glu Glu Tyr Asp Leu Gln Phe Ile Phe Gln Leu Cys Thr Ile Thr Leu
    370                 375                 380

Thr Ala Asp Val Met Ser Tyr Ile His Ser Met Asn Ser Ser Ile Leu
385                 390                 395                 400

Glu Asp Trp Asn Phe Gly Val Pro Pro Pro Pro Thr Thr Ser Leu Val
                405                 410                 415

Asp Thr Tyr Arg Phe Val Gln Ser Val Ala Ile Thr Cys Gln Lys Asp
            420                 425                 430

Ala Ala Pro Ala Glu Asn Lys Asp Pro Tyr Asp Lys Leu Lys Phe Trp
        435                 440                 445

Asn Val Asp Leu Lys Glu Lys Phe Ser Leu Asp Leu Asp Gln Tyr Pro
    450                 455                 460

Leu Gly Arg Lys Phe Leu Val Gln
465                 470
```

VACCINE AGAINST HPV16 AND HPV18 AND AT LEAST ANOTHER HPV TYPE SELECTED FROM HPV 31, 45 OR 52

This application is a 371 application of PCT/EP2005/006461 filed 14 Jun. 2005 which is a continuation-in-part of U.S. application Ser. No. 11/114,301 filed 26 Apr. 2005 and claims the benefit of GB application 0413510.9 filed 16 Jun. 2004.

BACKGROUND OF THE INVENTION

Papillomaviruses are small DNA tumour viruses, which are highly species specific. So far, over 100 individual human papillomavirus (HPV) genotypes have been described. HPVs are generally specific either for the skin (e.g. HPV-1 and -2) or mucosal surfaces (e.g. HPV-6 and -11) and usually cause benign tumours (warts) that persist for several months or years. Such benign tumours may be distressing for the individuals concerned but tend not to be life threatening, with a few exceptions.

Some HPVs are also associated with cancers, known as oncogenic HPV types. The strongest positive association between an HPV and human cancer is that which exists between HPV-16 and HPV-18 and cervical carcinoma. Cervical cancer is the most common malignancy in developing countries, with about 500,000 new cases occurring in the world each year.

Other HPVs of particular interest with respect to cancer are types 31, 33, 35, 39, 45, 51, 52, 56, 58, 59, 68, 73, 82, 26, 53, and 66.

HPV virus like particles (VLPs) have been suggested as potential vaccines for treatment of HPV. A bivalent vaccine utilizing VLPs has been shown to be effective in prevention of infection with HPV 16 and 18 types in young women (Lancet, vol 364, issue 9447, November 2004, pages 1757-1765).

There is still a need for a vaccine that protects against multiple (e.g. >2) HPV types.

The present invention addresses this need.

SUMMARY OF THE INVENTION

In a first aspect the present invention relates to an immunogenic composition comprising VLPs from HPV 16 and 18 and at least one other HPV cancer type, the other cancer type being selected from the list consisting of HPV types 31, 45 and 52, wherein the dose of the VLP of the at least one other cancer types is reduced relative to that of HPV 16 or 18.

In a related aspect the invention relates to an immunogenic composition comprising VLPs from HPV 16 and at least one other HPV cancer type, the other cancer type being selected from the list consisting of HPV types 31 and 52, wherein the dose of the VLP of the at least one other cancer types is reduced relative to that of HPV 16.

In a related aspect the invention relates to an immunogenic composition comprising VLPs from HPV 18 and HPV 45, wherein the dose of the HPV 45 VLP is reduced relative to that of HPV 18.

The invention further relates to an immunogenic composition as defined above in combination with an adjuvant and/or carrier.

The invention further relates to a vaccine comprising an immunogenic composition as defined above with a pharmaceutically acceptable excipient.

The invention further relates to a method of preventing HPV infection and/or disease comprising administering to an individual in need thereof a composition or vaccine as defined above.

The invention further relates to a method for making an immunogenic composition as defined above comprising mixing VLPs from HPV 16 and 18 with at least one other HPV cancer type, the other cancer type being selected from the list consisting of HPV types 31, 45, and 52, wherein the dose of the VLP of the at least one other cancer types is reduced relative to that of HPV 16 or 18.

The above aspects of the invention may also employ HPV capsomers rather than VLPs.

DETAILED DESCRIPTION

We have surprisingly determined that HPV 16 and 18 VLPs can provide cross protection against infection and/or disease by certain other HPV cancer types, that is HPV 31, HPV 45 and HPV 52. Data is provided in the examples herein.

Cross protection may be considered as the protection afforded by a vaccine containing one HPV type against infection (incident or persistent) and/or disease caused by a different HPV type. Incident and persistent infection are defined as in the Lancet paper by Harper et al. Vol 364, issue 9447, November 2004, pages 1757-1765. Cross protection may be assessed by considering the vaccine efficacy (V.E.), wherein the V.E. is the % improvement in protection against infection by the vaccine compared to a placebo group for a given type.

Accordingly HPV vaccines comprising HPV 16 and 18 VLPs can be formulated using a lower dose of other (non-HPV 16/18) cancer type VLPs (31, 45 or 52) than would otherwise be required in the absence of HPV 16 and 18 VLPs, whilst still achieving the same protective response against incident and/or persistent HPV infection for that other type. Reduction of the dose of other cancer type VLPs in a multivalent vaccine scenario, without significant impact on the protection caused by those other types, may be advantageous where the total amount of antigen may be limited; for example, by physical, chemical or regulatory constraints. It also allows more doses of a vaccine to be produced for a given quantity of antigen and can potentially reduce overall vaccine cost.

The dose of VLP herein is suitably the amount of VLP, measured by weight.

In other words, to achieve the same protective response against incident and/or persistent infection and/or disease, the dose of (non HPV 16/HPV 18) 'other cancer type' VLPs that need to be used in combination with HPV 16 and/or HPV 18 VLPs can be reduced compared to that level which is required in the absence of such type 16 and/or 18 VLPs.

The invention thus relates to an immunogenic composition comprising VLPs from HPV 16 and 18 and at least one other HPV cancer type, the other cancer type being selected from the list consisting of HPV types 31, 45, and 52, wherein the dose of the VLP of the at least one other cancer types is reduced relative to that of HPV 16 or 18.

In an alternative aspect the invention relates to an immunogenic composition comprising VLPs from HPV 16 and 18 and at least one other HPV cancer type, the other cancer type being selected from the list consisting of HPV types 31, 45 and 52, wherein the dose of the VLP of the at least one other cancer type is reduced relative to that which would otherwise be required, in the absence of HPV 16 and 18 VLPs, to generate the same protection against incident and/or persistent HPV infection by that other cancer type.

In one aspect the dose of the (non HPV 16, 18) other cancer type VLP is sufficient to provide protection against incident and/or persistent infection by that type, and in one aspect of the invention protection against at least incident infection.

In an aspect of the invention the composition of the invention is suitable for protection of infection and/or disease in human subjects.

A suitable dose can be determined by, for example, trials in humans such as those described in the examples herein.

Protection vs. incident and/or persistent infection by a given HPV type, such as HPV 16, 18, 31, 45 or 52 for example, is suitably protection in 50% of a vaccinated population against infection by that type, and in one aspect of the invention is 60% protection, in a further aspect 70% protection, in a further aspect 80% protection, in a further aspect 90% protection, in a further aspect 95% protection, in a further aspect 96% protection, in a further aspect 97% protection, in a further aspect 98% protection, in a further aspect 99% protection and in a yet further aspect 100% protection.

Suitably this protection is assessed over a period of at least 6 months, such as over a period of at least 9 months, at least 1 year, at least 18 months, suitably over a period of 2 years or greater than 2 years.

In one aspect of the invention the protection is seen against infection or disease caused by HPV 16 and/or HPV 18, and in one aspect both HPV 16 and HPV 18 infection and/or disease.

Prevention of infection may be assessed by analysis of HPV species present in vaccinated individuals, for example by PCR analysis and/or hybridization techniques such as those described in WO03014402 and WO9914377, incorporated herein by reference.

Where the immunogenic composition of the invention comprises both HPV 16 and 18 VLPs then the non HPV 16/18 cancer type VLPs is type 31, or type 45, or type 52, or a combination thereof. In one aspect the immunogenic composition of the invention comprises VLPs from HPV 16, 18, 31 and 45. In one aspect the immunogenic composition of the invention comprises VLPs from HPV 16, 18, 31 and 52. In one aspect the immunogenic composition of the invention comprises VLPs from HPV 16, 18, 45 and 52. In one aspect the immunogenic composition of the invention comprises VLPs from HPV 16, 18, 31, 52 and 45. Where there are 2 or more other cancer type VLPs (e.g. 31 and 45, 31 and 52, 45 and 52), then at least one of these other cancer types is present at a dose which is reduced to that of HPV 16 or HPV 18.

In one aspect the dose of HPV 31 is reduced relative to that of HPV 16.

In one aspect the dose of HPV 52 is reduced relative to that of HPV 16.

In one aspect the dose of HPV 45 is reduced relative to that of HPV 18.

Suitably the immunogenic compositions as defined above provide protection against incident infection and/or persistent infection and/or disease caused by HPV 16, HPV 18 and one or more of the other (31, 45 or 52) HPV types present in the groups listed above, such as incident infection.

Where an immunogenic composition of the invention comprises HPV 16 VLPs but not HPV 18 VLPs then suitably the non HPV 16/18 VLP cancer type is type 31 and/or type 52.

Where an immunogenic composition of the invention comprises HPV 18 VLPs but no HPV 16 VLPs then suitably the non HPV 16/18 VLP cancer type is type 45.

In an aspect of the invention the composition comprises HPV 16 and 18 VLPs in combination with either or both of HPV 31 and HPV 45 VLPs.

In an aspect of the invention the composition comprises at least HPV 16 VLPs in combination with HPV 31 VLPs.

The composition of the invention can comprise, in addition to VLPs at reduced dose, other HPV VLPs at any suitable dose. For example, the composition of the invention can comprise additional "high risk" cancer types such as one or more of HPV 33, 35, 39, 51, 56, 58, 59, 66, or 68.

In one aspect the composition can comprise additional so called "genital warts" types such as HPV 6 and/or 11, or so called "skin" types such as HPV 5 and/or 8. In one aspect the additional VLPs are present at the same dose or higher than HPV 16 and/or HPV 18.

In one aspect of the invention the composition comprises HPV 39 and/or HPV 51 VLPs, and the dose of at least one of these is reduced relative to HPV 16 and/or HPV 18.

In one aspect the amount of any additional VLP is selected so as to provide some degree of protection against infection or disease against the additional type(s).

Certain compositions of the invention, individualized below, comprise the following dose of VLPs:

| Composition number | HPV 16 VLP(μg) | HPV 18 VLP(μg) | HPV 31 VLP(μg) | HPV 45 VLP(μg) |
|---|---|---|---|---|
| 1 | 20 | 20 | 10 | 10 |
| 2 | 20 | 30 | 10 | 10 |
| 3 | 20 | 30 | 20 | 20 |
| 4 | 30 | 20 | 10 | 10 |
| 5 | 30 | 20 | 20 | 20 |

Suitably there is no significant or biologically relevant interference between HPV VLPs in the composition of the invention, such that the combined VLP vaccine of the invention is able to offer effective protection against infection by each HPV VLP type represented in the vaccine. Suitably the immune response against a given VLP type in the combination is at least 50% of the immune response of that same VLP type when measured individually, preferably 100% or substantially 100%. For responses to the HPV 16 and HPV 18 VLP components, the combined vaccine of the invention preferably stimulates an immune response which is at least 50% of that provided by a combined HPV 16/HPV 18 VLP vaccine. Suitably the immune response generated by the vaccine of the invention is at a level in which the protective effect of each VLP type is still seen. The immune response may suitably be measured, for example, by antibody responses using standard techniques such as ELISA, and by clinical trials as described herein.

In one aspect the composition of the invention does not comprise a heat shock protein or fragment thereof.

In one aspect the composition of the invention does not comprise an HPV L2 protein or peptide. In another aspect the composition of the invention does comprise an HPV L2 protein or peptide.

HPV VLPs and methods for the production of VLPs are well known in the art. VLPs typically are constructed from the L1 and optionally L2 structural proteins of the virus, see for example WO9420137, WO9629413 and WO9405792. Any suitable HPV VLP may be used in the present invention such as an L1 or L1+L2 VLP.

VLP formation can be assessed by standard techniques such as, for example, electron microscopy and dynamic laser light scattering.

In one aspect of the invention the VLP is an L1 only VLP.

The VLP may comprise full length L1 protein.

In an aspect of the invention the L1 protein used to form the VLP is a truncated L1 protein. Truncated HPV L1 proteins are disclosed in, for example, U.S. Pat. No. 6,361,778, incorporated herein by reference. In one aspect the truncation removes a nuclear localisation signal. In a further aspect the truncation is a C terminal truncation. In a further aspect the C terminal truncation removes less than 50 amino acids, suitably preferably less than 40 amino acids. Suitably the HPV 16 L1 sequence starts at the second methionine codon, for example as shown in the sequence below, or analogous positions in other HPV types. Where the VLP is an HPV 16 VLP then in one aspect the C terminal truncation removes 34 amino acids from HPV 16 L1 sequence. Where the VLP is an HPV 18 VLP then in one aspect the C terminal truncation removes 35 amino acids from the HPV 18 L1 sequence.

In one aspect the HPV 16 sequence is the following sequence:

```
MSLWLPSEATVYLPPVPVSKVVSTDEYVARTNIYYHAGTSRLLAVGHPYFPIKKPNNNKI    60
LVPKVSGLQYRVFRIHLPDPNKFGFPDTSFYNPDTQRLVWACVGVEVGRGQPLGVGISGH    120
PLLNKLDDTENASAYAANAGVDNRECISMDYKQTQLCLIGCKPPIGEHWGKGSPCTNVAV    180
NPGDCPPLELINTVIQDGDMVDTGFGAMDFTTLQANKSEVPLDICTSICKYPDYIKMVSE    240
PYGDSLFFYLRREQMFVRHLFNRAGAVGENVPDDLYIKGSGSTANLASSNYFPTPSGSMV    300
TSDAQIFNKPYWLQRAQGHNNGICWGNQLFVTVVDTTRSTNMSLCAAISTSETTYKNTNF    360
KEYLRHGEEYDLQFIFQLCKITLTADVMTYIHSMNSTILEDWNFGLQPPPGGTLEDTYRF    420
VTSQAIACQKHTPPAPKEDPLKKYTFWEVNLKEKFSADLDQFPLGRKFLLQ            471
```

The HPV 16 sequence may also be that disclosed in WO9405792 or U.S. Pat. No. 6,649,167, for example, suitably truncated. Suitable truncates are truncated at a position equivalent to that shown above, as assessed by sequence comparison.

In one aspect the HPV 18 sequence is the following sequence:

```
MALWRPSDNTVYLPPPSVARVVNTDDYVTRTSIFYHAGSSRLLTVGNPYFRVPAGGGNKQ    60
DIPKVSAYQYRVFRVQLPDPNKFGLPDNSIYNPETQRLVWACVGVEIGRGQPLGVGLSGH    120
PFYNKLDDTESSHAATSNVSEDVRDNVSVDYKQTQLCILGCAPAIGEHWAKGTACKSRPL    180
SQGDCPPLELKNTVLEDGDMVDTGYGAMDFSTLQDTKCEVPLDICQSICKYPDYLQMSAD    240
PYGDSMFFCLRREQLFARHFWNRAGTMGDTVPPSLYIKGTGMRASPGSCVYSPSPSGSIV    300
TSDSQLFNKPYWLHKAQGHNNGVCWHNQLFVTVVDTTRSTNLTICASTQSPVPGQYDATK    360
FKQYSRHVEEYDLQFIFQLCTITLTADVMSYIHSMNSSILEDWNFGVPPPPTTSLVDTYR    420
FVQSVAITCQKDAAPAENKDPYDKLKFWNVDLKEKFSLDLDQYPLGRKFLVQ           472
```

An alternative HPV 18 sequence is disclosed in WO9629413, which may be suitably truncated. Suitable truncates are truncated at a position equivalent to that shown above, as assessed by sequence comparison.

Other HPV 16 and HPV 18 sequences are well known in the art and may be suitable for use in the present invention.

Suitable truncations of HPV 31, HPV 45 and HPV 52 may also be made, suitably removing equivalent C terminal portions of the L1 protein to those described above as assessed by sequence alignment.

Truncated L1 proteins are disclosed in, for example, WO9611272 and U.S. Pat. No. 6,066,324, herein incorporated by reference.

In one aspect truncated L1 proteins are suitably functional L1 protein derivatives, capable of raising an immune response (if necessary, when suitably adjuvanted), said immune response being capable of recognising a VLP consisting of the full length L1 protein and/or the HPV type from which the L1 protein was derived.

VLPs of the invention may also comprise other types of functional protein derivatives, including mutants of the full length or truncated HPV L1 proteins such as deletion, substitution, or insertion mutants. The L1 protein or derivative may also be a fusion protein, such as the fusion of the L1 protein with L2 or an early protein. The L1 protein or functional protein derivative is able to form a VLP, and VLP formation can be assessed by standard techniques such as, for example, electron microscopy and dynamic laser light scattering.

VLPs may be made in any suitable cell substrate such as yeast cells or insect cells e.g. baculovirus cells, and techniques for preparation of VLPS are well known in the art, such as WO9913056 and U.S. Pat. No. 6,245,568, and references therein, the entire contents of which are hereby incorporated by reference.

In one aspect VLPs are made by disassembly and reassembly techniques, which can provide for more stable and/or homogeneous papillomavirus VLPs. For example, McCarthy et al, 1998 "Quantitative Disassembly and Reassembly of Human Papillomavirus Type 11 Viruslike Particles in Vitro" J. Virology 72(1):33-41, describes the disassembly and reassembly of recombinant L1 HPV 11 VLPs purified from insect cells in order to obtain a homogeneous preparation of VLP's. WO9913056 and U.S. Pat. No. 6,245,568 also describe disassembly/reassembly processes for making HPV VLPs.

In one aspect the HPV VLPS of the invention are made as described WO9913056 or U.S. Pat. No. 6,245,568.

The VLPs of the invention may be combined with an adjuvant or imunostimulant such as, but not limited to, detoxified lipid A from any source and non-toxic derivatives of lipid A, saponins and other reagents capable of stimulating a TH1 type response.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of bacterial endotoxins, Plenum Publ. Corp., NY, p 407-419) and has the following structure:

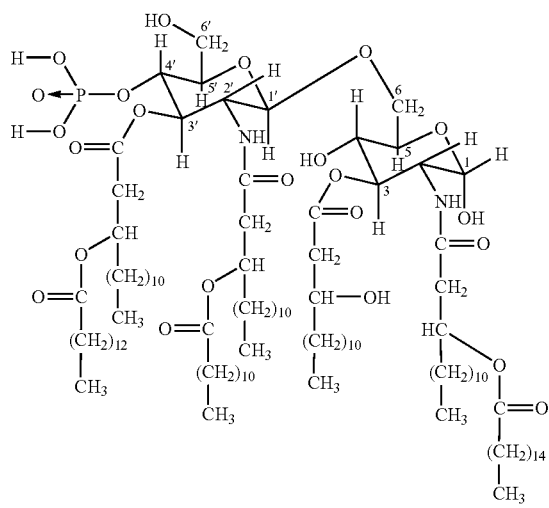

A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof.

In one aspect the 3D-MPL is in the form of an emulsion having a small particle size less than 0.2 μm in diameter, and its method of manufacture is disclosed in WO 94/21292. Aqueous formulations comprising monophosphoryl lipid A and a surfactant have been described in WO9843670A2.

The bacterial lipopolysaccharide derived adjuvants to be formulated in the compositions of the present invention may be purified and processed from bacterial sources, or alternatively they may be synthetic. For example, purified monophosphoryl lipid A is described in Ribi et al 1986 (supra), and 3-O-Deacylated monophosphoryl or diphosphoryl lipid A derived from *Salmonella* sp. is described in GB 2220211 and U.S. Pat. No. 4,912,094. Other purified and synthetic lipopolysaccharides have been described (Hilgers et al., 1986, *Int.Arch.Allergy.Immunol.*, 79(4):392-6; Hilgers et al., 1987, Immunology, 60(1):141-6; and EP 0 549 074 B1). In one aspect the bacterial lipopolysaccharide adjuvant is 3D-MPL.

Accordingly, the LPS derivatives that may be used in the present invention are those immunostimulants that are similar in structure to that of LPS or MPL or 3D-MPL. In another aspect of the present invention the LPS derivatives may be an acylated monosaccharide, which is a sub-portion to the above structure of MPL.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja Saponaria Molina), and fractions thereof, are described in US 5,057,540 and "Saponins as vaccine adjuvants", Kensil, C. R., *Crit Rev Ther Drug Carrier Syst*, 1996, 12 (1-2):1-55; and EP 0 362 279 B1. Particulate structures, termed Imune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Other saponins which have been used in systemic vaccination studies include those derived from other plant species such as Gypsophila and Saponaria (Bomford et al., Vaccine, 10(9): 572-577, 1992).

An enhanced system involves the combination of a non-toxic lipid A derivative and a saponin derivative particularly the combination of QS21 and 3D-MPL as disclosed in WO 94/00153, or a less reactogenic composition where the QS21 is quenched with cholesterol as disclosed in WO 96/33739.

In one aspect the adjuvant is a particularly potent adjuvant formulation involving QS21 and 3D-MPL in an oil in water emulsion is described in WO 95/17210.

Accordingly in one embodiment of the present invention there is provided a composition adjuvanted with detoxified lipid A or a non-toxic derivative of lipid A, more preferably adjuvanted with a monophosphoryl lipid A or derivative thereof.

In one aspect the composition additionally comprises a saponin, more preferably QS21.

In one aspect the adjuvant formulation additionally comprises an oil in water emulsion. The present invention also provides a method for producing a vaccine formulation comprising mixing a VLP present invention together with a pharmaceutically acceptable excipient, such as 3D-MPL.

Additional components that are preferably present in an adjuvanted composition according to the invention include non-ionic detergents such as the octoxynols and polyoxyethylene esters as described herein, particularly t-octylphenoxy polyethoxyethanol (Triton X-100) and polyoxyethylene sorbitan monooleate (Tween 80); and bile salts or cholic acid derivatives as described herein, in particular sodium deoxycholate or taurodeoxycholate. In one aspect the adjuvant formulation comprises 3D-MPL, Triton X-100, Tween 80 and sodium deoxycholate, which may be combined with an HPV VLP to provide a suitable vaccine.

In one embodiment of the present invention, the composition comprises a vesicular adjuvant formulation comprising cholesterol, a saponin and an LPS derivative. In this regard the adjuvant formulation can comprise a unilamellar vesicle comprising cholesterol, having a lipid bilayer suitably comprising dioleoyl phosphatidyl choline, wherein the saponin and the LPS derivative are associated with, or embedded within, the lipid bilayer. More preferably, these adjuvant formulations comprise QS21 as the saponin, and 3D-MPL as the LPS derivative, wherein the ratio of QS21:cholesterol is from 1:1 to 1:100 weight/weight, and most preferably 1:5 weight/weight. Such adjuvant formulations are described in EP 0 822 831 B, the disclosure of which is incorporated herein by reference.

In one aspect the compositions of the invention are used in combination with aluminium, and are suitably adsorbed or partially adsorbed onto aluminium adjuvants. Suitably the adjuvant is an aluminium salt, which in one aspect is in combination with 3D MPL, such as aluminium phosphate and 3D MPL. In another aspect the adjuvant is aluminium hydroxide, optionally in combination with 3D MPL.

In another aspect the composition is the combination of VLPs with an aluminium salt or with an aluminium salt +3D MPL. In an aspect of the invention the aluminium salt is aluminium hydroxide.

The composition of the invention may also comprise aluminium or an aluminium compound as a stabiliser.

The present invention generally relates to combinations of VLPs. However, it is appreciated that the essential component of the VLP is an L1 protein. L1 proteins associate to form pentamers (capsomers) which then tessellate (assemble) to form VLPs. As such the present invention relates also to immunogenic compositions as described above comprising L1 proteins, or capsomers comprising L1 proteins, in the place of VLPs as described herein. Suitably the L1 proteins are capable of stimulating a protective immune response. Suitably the L1 proteins are conformationally correct.

For the avoidance of doubt the invention thus also relates to the use of functional L1 derivatives as described above, such as L1 truncates, deletion, substitution or insertion mutants, and fusion proteins, suitably those which are capable of provoking an immune response capable of recognising an HPV virus. Capsomers comprising such proteins are also included in the present invention. Capsomers as immunogenic agents are described in, for example, WO0204007. WO9901557 also discloses HPV capsomer containing compositions. L1 proteins, derivatives and capsomers may be used in the same way as described for VLPs above.

Thus the invention can be seen to relate to an immunogenic composition comprising an L1 protein, or functional derivative thereof, from HPV 16 and 18 and at least one other HPV cancer type, the other cancer type being selected from the list consisting of HPV types 31, 45 and 52, wherein the dose of the L1 protein, or derivative thereof, of the at least one other cancer type is reduced relative to that of HPV 16 or 18.

Thus the invention can be seen to relate to an immunogenic composition comprising an HPV capsomer from HPV 16 and 18 and at least one other HPV cancer type, the other cancer type being selected from the list consisting of HPV types 31, 45 and 52, wherein the dose of the capsomer of the at least one other cancer type is reduced relative to that of HPV 16 or 18.

In one aspect the invention relates to an immunogenic composition as discussed above in combination with a pharmaceutically acceptable excipient. Suitable excipients are well known in the art and include buffers and water, for example.

The compositions and vaccines of the invention may be provided and delivered by any of a variety of routes such as oral, topical, subcutaneous, mucosal (typically intravaginal), intraveneous, intramuscular, intranasal, sublingual, intradermal and via suppository.

In one aspect of the invention the composition or vaccine may be formulated or co-administered with an HPV early antigen, for example an antigen selected from the list consisting of HPV E1, E2, E3, E4, E5, E6, E7 and E8. In an alternative aspect the vaccine may lack an HPV early antigen, for example an antigen selected from the list consisting of HPV E1, E2, E3, E4, E5, E6, E7 and E8.

Optionally the composition or vaccine may also be formulated or co-administered with non-HPV antigens. Suitably these non-HPV antigens can provide protection against other diseases, most preferably sexually transmitted diseases such as herpes simplex virus, EBV, chlamydia and HIV. We particularly prefer that the composition or vaccine comprises gD or a truncate thereof from HSV, suitably a C terminal truncate from HSV-2 known as gD2t. In this way the composition or vaccine provides protection against both HPV and HSV.

The dosage of the composition or vaccine components will vary with the condition, sex, age and weight of the individual, the administration route and HPV of the vaccine. The quantity may also be varied with the number of VLP types. Suitably the delivery is of an amount of vaccine suitable to generate an immunologically protective response. Suitably each vaccine dose comprises 1-100 µg of each VLP, in one aspect 5-80 µg, in a further aspect 5-30 µg each VLP, in a further aspect 5-20 µg of each VLP with yet further aspects being specifically 5 µg, 6 µg, 10 µg, 15 µg or 20 µg.

Doses suitable for use in humans typically include 20-40 µg of HPV 16 and HPV 18 VLPs, with reduced doses of the other HPV cancer types (31, 45, 52) as described herein, suitably at a level of less than 20 jig per VLP, suitably at a level that is able to provoke a protective immune response in at least some vaccinated individuals.

Other doses suitable for use in humans may comprise lower quantities of HPV 16 and/or 18, provided such doses are protective in humans as can be assessed using trials outlined herein. Such doses may be appropriate where the VLPs of the invention are combined with strong adjuvants, for example.

In one aspect the composition of the invention comprises 20 µg of HPV 16, 20 µg of HPV 18 and between 5-18 µg of each VLP from the other cancer type (31, 45 or 52), for example 5-15 µg, and in a further aspect specifically 5, 6, 7, 8, 9, 10, 11, 12, 13, 14 or 15 µg of VLP from each non HPV 16/18 cancer type.

In one aspect the composition of the invention comprises 10-15 µg of HPV 16, 10-15 µg of HPV 18 and between 5-9 µg of each VLP from the other cancer type (31, 45 or 52), and in one aspect specifically 5, 6, 7, 8 or 9 µg of VLP from each non HPV 16/18 cancer type.

In one aspect the ratio by weight of HPV 16 VLP to other cancer type (31, 45 or 52) VLP is in the range of 1:0.9-1:0.1 (HPV 16: other type), suitably in the range of 1:0.9-1:0.3, suitably 1:0.8-1:0.4.

In one aspect the ratio by weight of HPV 18 VLP to other cancer type (31, 45 or 52) VLP is from 1:0.9-1:0.1, (HPV 18: other type), suitably in the range of 1:0.9-1:0.3, suitably 1:0.8-1:0.4.

In other words, a reduced dose is suitably 10-90% of the dose of HPV 16 or HPV 18 VLPs, and in one aspect is 20-80% of the dose of HPV 16 or HPV 18 VLPs, in a further aspect 30-70%, in a yet further aspect 30-60%, and specifically 10%, 20%, 30%, 40%, 50%, 60%, 70%, 80% or 90% of the HPV 16 or HPV 18 dose.

In one aspect the composition is suitably used to prevent one or more of: HPV-16 and/or HPV-18 infection, persistent HPV-16 and/or HPV-18 infection and HPV-16 and/or HPV-18 associated cervical neoplasia.

Suitably the use of the immunogenic composition of the invention is used to prevent cervical neoplasia and/or incident infection and/or persistent infection associated with infection by other (non HPV 16, 18) oncogenic types.

Suitably the immunogenic composition of the invention is used in the active immunization of adults and adolescent females from the age of 10 years onwards. For all compositions and vaccines of the invention the composition or vaccine is suitably used for the vaccination of adolescent girls aged 10-15, preferably 10-13 years. The composition or vaccine may also be administered to older adult women following an abnormal pap smear or after surgery following removal of a lesion caused by HPV, or who are seronegative and DNA negative for HPV cancer types. Females of 10-55 years are another suitable target group. In another aspect the vaccine may be used in girls and women of all ages, from infants upwards, and in a further aspect may be given to boys or men. In a further aspect the vaccine may be used therapeutically in women who are seropositive for the HPV virus.

In one aspect the composition of the invention is used to prevent or treat cervical cancer, or CIN 1, CIN II or CIN III disease states caused by HPV infection.

In one aspect the vaccine is delivered in a 2 or 3 dose regime, for example in a 0, 1 month regime or a 0, 2 month regime, or a 0, 2, 6 month regime or a 0,1 and 6 month regime respectively. Suitably the vaccination regime incorporates a booster injection after 3 to 10 years, or 5-10 years, such as preferably 3, 4, 5, 6, 7, 8, 9 or 10 years.

In one aspect the composition or vaccine of the invention is a liquid vaccine formulation, although the vaccine may be lyophilised and reconstituted prior to administration. Topical formulations such as intravaginal creams may also be used, for example.

The teaching of all references in the present application, including patent applications and granted patents, are herein fully incorporated by reference.

The compositions and vaccines of the invention comprise certain HPV components as laid out above. In a further aspect of the invention the vaccine consists essentially of, or consists of, said components.

The present invention is hereby illustrated by reference to the following non-limiting examples relating to the cross protection by HPV 16 and HPV 18 VLPs, and showing production of HPV VLPs:

EXAMPLE 1

Healthy women between the ages of 15 and 25 years were immunised with a mixture of HPV 16 and HPV 18 L1 VLPs. The women at enrolment were: 1) seronegative for HPV-16 and HPV-18; 2) negative for high risk HPV infection of the cervix (detected by HPV PCR); 3) had 6 or fewer lifetime sexual partners and 4) had normal PAP smears.

The mixture comprised, per 0.5 ml dose, 20 µg of HPV-16 L1 VLP, 20 µg of HPV-18 L1 VLP and was adjuvanted with 500 µg of aluminum hydroxide and 50 µg of 3D MPL. The placebo group was injected with 500 µg of aluminum hydroxide alone.

The vaccine efficacy (V.E.) against high risk cancer HPV types was assessed, wherein the V.E. is the % improvement in protection against infection by the vaccine compared to a placebo group.

Cross protection was assessed by detecting the presence of nucleic acid specific for various oncogenic types in the vaccinees and control group. Detection was carried out using techniques as described in WO03014402, and references therein, particularly for non-specific amplification of HPV DNA and subsequent detection of DNA types using a LiPA system as described in WO 99/14377, and in Kleter et al, [Journal of Clinical Microbiology (1999), 37 (8): 2508-2517], the whole contents of which are herein incorporated by reference.

Any suitable method can, however, be used for the detection of HPV DNA in a sample, such as type specific PCR using primers specific for each HPV type of interest. Suitable primers are known to the skilled person, or can be easily constructed given that the sequences of the oncogenic HPV types are known.

Vaccine efficacy was assessed against infections for all of the 12 high risk cancer types, HPV-16 phylogenetic-related types (the groups of; 31, 35, and 58; 31, 33, 35, 52 and 58) and HPV-18 phylogenetic related types (45 and 59).

An initial analysis was carried out on an "ITT" (Intention To Treat cohort, representing all individuals who received at least one dose of vaccine). This data is shown in Table 1.

The results presented in Tables 2 and 3 relate to the "ATP" (According To Protocol) group for those patients who complied with all the criteria of the trial. Table 2 is a midpoint analysis with data taken from all patients at the timepoint at which at least 50% of the cohort were 18 months after their first vaccination. Table 3 gives the final results, all data being from subjects at 18 months post first vaccination (month 0). In the ATP group all patients received 3 doses of vaccine at 0, 1 and 6 months and were seronegative at 6 months.

As demonstrated by the data presented in table 1, immunization with a mixture of HPV16 and HPV18 VLPs provided apparent cross-protection against other HPV types. At this point the sample sizes are too small to provide for a rigorous statistical analysis, however the data demonstrate a positive trend and suggest that immunization with HPV16 and HPV18 VLPs will be efficacious against infection with other HPV types.

This was confirmed as the study progressed.

Details of the protocol are described further in Example 3.

Table 2 demonstrates that HPV 16 and HPV 18 provide statistically significant cross protection against the group of high risk cancer types 31, 33, 35, 39, 45, 51, 52, 56, 58, 59, 66 and 68.

Table 3 demonstrates that, except for the HPV-18 related types (which show a very strong trend), there is statistically significant cross-protection against the groups of: HPV 31, 35, 58; HPV 31, 33, 35, 52, 58; and the 12 high risk (non HPV-16/18) types evaluated.

Later analysis of the trial data has indicated that the combined HPV 16 and 18 vaccine used in Examples 1 provides statistically significant cross protection against statistical incident infection by HPV 31 (vaccine efficacy 75.1%, p=0.007). While the sample size does not yet allow for statistically significant conclusions to be drawn on other types, the data on other types such as 39, 45, 51 and 52 demonstrate a positive trend and suggest that immunization with HPV16 and HPV18 VLPs will be efficacious against infection with other HPV types.

Data presented in Example 3 provides further data obtained in the same study, and focuses on cross protection provided against certain specific types.

TABLE 1

| HPV types analysed | Number of women infected (vaccine group) | % women infected (vaccine group) = A | Number of women infected (placebo group) | % women infected (placebo group) = B | % vaccine efficacy 1 − (A/B) × 100, adjusted for relative size of vaccine and placebo group | 95% confidence limits -lower limit | 95% confidence limits -upper limit | P |
|---|---|---|---|---|---|---|---|---|
| HPV 31, 35, 58 | 5 | 1.1 | 11 | 2.4 | 55.1 | −29.1 | 84.4 | 0.127 |
| HPV 31, 33, 35, 52, 58 | 17 | 3.8 | 24 | 5.4 | 30.3 | −29.7 | 62.6 | 0.252 |
| HPV 45, 59 | 3 | 0.7 | 6 | 1.3 | 50.6 | −97.7 | 87.6 | 0.309 |
| HPV 31, 33, 35, 39, 45, 51, 52, 56, 58, 59, 66, 68. | 27 | 6.3 | 40 | 9.4 | 34.6 | −6.5 | 59.9 | 0.086 |

Samples were taken at 9, 12, 15 and 18 months from patients and tested for HPV infection by the types specified above.

TABLE 2 vaccine efficacy after three doses in preventing incident heterologous infections.
Table 2: Vaccine efficacy against infection with HPV-16 phylogenetically related types, HPV-18 phylogenetically related types, HPV-16 and/or HPV-18 phylogenetically related types and all high-risk types exclusive of HPV-16 and HPV-18 - ATP cohort (month 6-18)

| | Attack rate | | | | | | Vaccine efficacy | | |
|---|---|---|---|---|---|---|---|---|---|
| | Vaccine | | | Placebo | | | | | |
| Infection Type | N | n | AR | N | n | AR | % | 95% CI | p-value |
| HPV-16 related | 433 | 12 | 2.8 | 438 | 24 | 5.5 | 49.4 | 0.2  74.4 | 0.060 |
| HPV-16 related* | 423 | 29 | 6.9 | 423 | 46 | 10.9 | 37.0 | 1.6  59.6 | 0.052 |
| HPV-18 related | 442 | 9 | 2.0 | 449 | 16 | 3.6 | 42.9 | −27.9  74.5 | 0.223 |
| HPV-16/18 related | 433 | 21 | 4.9 | 438 | 41 | 9.4 | 48.2 | 13.8  68.9 | 0.012 |
| HPV-16/18 related* | 423 | 34 | 8.0 | 423 | 56 | 13.2 | 39.3 | 9.0  59.5 | 0.019 |
| High-risk** | 385 | 53 | 13.8 | 386 | 88 | 22.8 | 39.6 | 17.7  55.7 | 0.001 |

N = number of subjects in specific cohort
n = number of subjects with incident HPV infection
AR = Attack rate = n/N
95% CI = 95% confidence interval
lower limit = 1 − exp (log (arv/arp) + 1.96 * sqrt (1/nv − 1/Nv + 1/np − 1/Np))
upper limit = 1 − exp (log (arv/arp) − 1.96 * sqrt (1/nv − 1/Nv + 1/np − 1/Np))
when number of cases in vaccine = 0:
lower limit* = 1 − exp (log (arv*/arp*) + 1.96 * sqrt (1/(nv + 0.5) − 1/(Nv + 0.5) + 1/(np + 0.5) - 1/(Np + 0.5)))
upper limit* = 1 − exp (log (arv*/arp*) − 1.96 * sqrt (1/(nv + 0.5) − 1/(Nv + 0.5) + 1/(np + 0.5) − 1/(Np + 0.5)))
with: arv = attack rate in vaccine recipients
arp = attack rate in placebo recipients
nv = number of cases in vaccine recipients
Nv = number of cases and non-cases in vaccine recipients
np = number of cases in placebo recipients
Np = number of cases and non-cases in placebo recipients
HPV-16 related: HPV-16 phylogenetically related types 35, 31, 58 without considering other HPV types
HPV-16 related*: HPV-16 phylogenetically related types 35, 31, 58, 33, 52 without considering other HPV types
HPV-18 related: HPV-18 phylogenetically related types 45, 59 without considering other HPV types
HPV-16 and/or HPV-18 related: HPV-16 and/or HPV-18 phylogenetically related types 35, 31, 58, 45, 59 without considering other HPV types
HPV-16 and/or HPV-18 related*: HPV-16 and/or HPV-18 phylogenetically related types 35, 31, 58, 33, 52, 45, 59 without considering other HPV types
**= High-risk types exclusive of HPV-16 and HPV-18

TABLE 3

| HPV types analysed | Total number of number of subjects with information available per group | Number of women infected (vaccine group) | % women infected (vaccine group) = A | Number of women infected (placebo group) | % women infected (placebo group) = B | % vaccine efficacy 1 − (A/B) × 100, adjusted for relative size of vaccine and placebo group | 95% confidence limits -lower limit | 95% confidence limits -upper limit | P |
|---|---|---|---|---|---|---|---|---|---|
| HPV 31, 35, 58 | 412 | 11 | 2.7 | 26 | 6.3 | 57.9 | 15.9 | 78.9 | 0.012 |
| HPV 31, 33, 35, 52, 58 | 403 | 28 | 6.9 | 48 | 12.2 | 43.0 | 11.0 | 63.5 | 0.015 |
| HPV 45, 59 | 421 | 10 | 2.4 | 15 | 3.6 | 33.5 | −46.3 | 69.8 | 0.319 |
| HPV 31, 33, 35, 39, 45, 51, 52, 56, 58, 59, 66, 68. | 368 | 58 | 15.8 | 90 | 25.3 | 37.7 | 16.2 | 53.6 | 0.002 |

Samples were taken at 18 months from patients and tested for HPV infection by the types specified above.

EXAMPLE 2

HPV 16 and HPV 18 VLPs may be produced in the following manner:

EXAMPLE 1

The combination of HPV 16 and HPV 18 L1 VLPs is detailed herein. L1 proteins from other HPV genotypes may be readily produced by similar methods, already known in the art.

A Preparation of HPV 16/18 L1 VLPs

Production of HPV 16 and HPV 18 VLPs was carried out using standard protocols—for example, see WO9913056. HPV 16/18 proteins were expressed in *Trichoplusia ni* (High Five™) cells (at a density of ~350000 cells/ml) infected with recombinant Baculovirus (MOI of 0.3) encoding the HPV 16 or 18 L1 gene of interest. Cells were harvested approximately 72 hours post infection.

4.1 B Cell Harvest/Antigen Extraction

The antigen (L1-16/18) was extracted from Hi5 cells in a three step process of concentration, extraction, clarification. The concentration step removes up to 90% of the culture medium, and was performed by tangential flow filtration. The extraction step was performed with a hypotonic buffer (Tris 20 mM, pH 8.5). A volume equal to the culture volume was used to perform the extraction. A contact time of minimum half an hour under smooth agitation was used. The clarification was performed by tangential flow filtration.

C Purification

The purification process was carried out at room temperature. β-mercaptoethanol (4% w/w) was added to the extract in order to disassemble the VLP's into capsomers, for both antigens, L1-16/18. Glycerol was added up to a concentration of w/w 10% just prior to the addition of β-mercaptoethanol.

All buffers used were filtered on 0.22 μm filters prior to storage at 2° C.-8° C. Prior to each purification run, gel matrixes are sanitised and equilibrated with appropriate buffer before sample loading.

Purification regimes are given for the separate purification of L1 from both HPV 16 and 18. These schemes are broadly similar, and involve the steps of:

Anion exchange chromatography (Di methyl amino ethyl—DMAE),
Anion exchange chromatography (tri methyl amino ethyl—TMAE),
Hydroxyapatite chromatography,
Nanometric filtration (Planova),
Ultrafiltration,
Hydrophobic interaction chromatography (using Octyl Sepharose) for HPV 18 or Anion exchange chromatography (DEAE) for HPV 16; and
Sterile filtration.
4.1.1 Specifically:
4.1.2 C1 Purification of L1-18 antigen
4.1.2.1 Anion Exchange Chromatography DMAE The clarified extract (protein at a concentration of ~1 g/ml, with the L1 protein at ~150 mg/ml) is applied to an anion exchange column (Di Methyl Amino Ethyl). Elution is performed with (Tris 20 mM|NaCl 200 mM|4% β-mercaptoethanol BME) buffer, pH 7.9±0.2. The antigen is eluted in approximately 5 column volumes and the elution profile is monitored at 280 nm.

4.1.2.2 Anion Exchange Chromatography TMAE

The eluate of the first step is diluted with 1 volume of $H_2O$/BME 4%. The diluted eluate is then applied to a second anion exchange column (Tri Methyl Amino Ethyl). Elution is performed with (20 mM Tris|NaCl 200 mM|4% BME) buffer, pH 7.9±0.2.

The antigen is eluted in approximately 4 column volumes and the elution profile is monitored at 280 nm.

4.1.2.3 Hydroxyapatite Chromatography

The eluate of the TMAE step is applied to a hydroxyapatite (HA) column.

After sample application, the gel is eluted with approximately 2.5 column volumes of ($NaH_2PO_4$ 100 mM|NaCl 30 mM|4% BME) buffer, pH 6.0±0.2.

4.1.2.4 Nanometric Filtration (Planova)

The HA eluate is diluted in order to reach the following conditions: ($NaH_2PO_4$ 25 mM|NaCl 10 mM|4% BME) buffer, pH 7.5×0.2.

Then it is filtered successively on a 0.2 μm prefilter and on a Planova 15N filter of 0.12 $m^2$. The filtration is performed at constant pressure 200 mbar±20 mbar.

4.1.2.5 Ultrafiltration

The ultrafiltration is performed with a tangential flow ultrafiltration system equipped with polyethersulfone membranes (Centramate cassette 0.1 $m^2$, 100 kD).

The Planova eluate is treated to reach the following conditions: ($NaH_2PO_4$ 100 mM|NaCl 30 mM|4% BME), pH 6.0±0.2; then it is loaded in the system, concentrated 5 fold and dia-filtrated with continuous injection of ~10 starting volumes of (NaH$_2$PO$_4$ 20 mM|NaCl 500 mM) buffer, pH 6.0±0.2.

4.1.2.6 Hydrophobic Interaction Chromatography (Octyl Sepharose)

The ultrafiltration permeate is applied to an Octyl Sepharose column.

This chromatography step is run in the negative mode with approximately 5 column volumes of (Na$_3$PO$_4$ 20 mM|NaCl 500 mM) buffer, pH 6.0±0.2.

4.1.2.7 Sterile Filtration

The purified L1-18 antigen solution is sterilised by filtration on a 0.22 μm membrane.

4.1.3

4.1.4 C2 Purification of L1-16 Antigen 4.1.4.1 Anion Exchange Chromatography DMAE The clarified extract is applied to an anion exchange column (Di Methyl Amino Ethyl). Elution is performed with (Tris 20 mM|NaCl 180 mM|4% BME) buffer, pH 7.9±0.2.

The antigen is eluted in approximately 4 column volumes and the elution profile is monitored at 280 nm.

4.1.4.2 Anion Exchange Chromatography TMAE

The eluate of the first step is diluted with 1 volume of H$_2$O/BME 4%. The diluted eluate is then applied to a second anion exchange column (Tri Methyl Amino Ethyl).

Elution is performed with (20 mM Tris|NaCl 180 mM|4% BME) buffer, pH 7.9±0.2. The antigen is eluted in approximately 5 column volumes and the elution profile is monitored at 280 nm.

4.1.4.3 Hydroxyapatite Chromatography (HA)

The eluate of the TMAE step is applied to a HA column.

After sample application, the gel is eluted with approximately 3 column volumes of (NaH$_2$PO$_4$ 100 mM|NaCl 30 mM|4% BME) buffer, pH 6.0±0.2.

4.1.4.4 Nanometric Filtration (Planova)

The HA eluate is diluted in order to reach the following conditions: (NaH$_2$PO$_4$ 25 mM|NaCl 100 mM|4% BME) buffer, pH 7.5±0.2.

Then it is filtered successively on a 0.2 μm prefilter and on a Planova 15N filter of 0.12 m$^2$. The filtration is performed at constant pressure 200 mbar±20 mbar.

4.1.4.5 Ultrafiltration

The ultrafiltration is performed with a tangential flow ultrafiltration system equipped with polyethersulfone membranes (Centramate cassette 0.1 m$^2$, 100 kD).

The Planova eluate is treated to reach the following conditions: (NaH$_2$PO$_4$ 100 mM|NaCl 30 mM|4% BME), pH 6.0±0.2; then it is loaded in the system, concentrated 5 fold and dia-filtrated with continuous injection of ~10 starting volumes of (NaH$_2$PO$_4$ 20 mM|NaCl 500 mM) buffer, pH 6.0±0.2.

4.1.4.6 Anion Exchange Chromatography DEAE

The ultrafiltration eluate is adjusted to the conductivity of the equilibrium buffer, (Na$_3$PO$_4$ 20 mM|NaCl 250 mM), pH 6.0±0.2 and applied on an anion exchange column (Di Ethyl Amino Ethyl).

Elution is performed with (NaH$_2$PO$_4$ 20 mM|NaCl 500 mM) buffer, pH 6.0±0.2. The antigen is eluted in approximately 3 column volumes and the elution profile is monitored at 280 nm.

4.1.4.7 Sterile Filtration

The purified L1-16 antigen solution is sterilised by filtration on a 0.22 μm membrane.

C3

Each VLP type is adsorbed independently to produce a concentrated adsorbed monovalent.

Preparation of VLP16 Concentrated Adsorbed Monovalent:

60 μg of purified VLPs from HPV16 are adsorbed on 150 μg Al$^{3+}$ from Al(OH)$_3$, at a pH of 6.0±0.2, for one hour at room temperature with gentle stirring. This concentrated adsorbed monovalent is stored at +4° C. Adsorption is checked by centrifuging the preparation and quantifying VLPs in the supernatant.

Preparation of VLP18 Concentrated Adsorbed Monovalent:

60 μg of purified VLPs from HPV18 are adsorbed on 150 μg Al$^{3+}$ from Al(OH)$_3$, at a pH of 6.0±0.2, for one hour at room temperature with gentle stirring. This concentrated adsorbed monovalent is stored at +4° C. Adsorption is checked by centrifuging the preparation and quantifying VLPs in the supernatant.

D Final Vaccine Preparation:

Concentrated adsorbed monovalents prepared by the above method may be combined to form a suspension containing 20 μg each VLP per dose. Final vaccine is stored at +4° C.

Addition of VLPs from other cancer types may be added as appropriate, at suitable concentration in accordance with the invention. Sequences of such types are well known in the art and VLPs comprising such proteins can be readily expressed by the skilled person.

The combined adsorbed bulks, or individual adsorbed bulks, may be further mixed with adjuvants such as 3D-MPL.

EXAMPLE 3

Precise details of the experiment carried out are provided in Harper et al, the Lancet. 2004 Nov. 13;364(9447):1757-65.

In summary, healthy women between the ages of 15 and 25 years were immunised with a mixture of HPV 16 and HPV 18 L1 VLPs. The women at enrolment were: 1) seronegative for HPV-16 and HPV-18; 2) negative for high risk HPV infection of the cervix (detected by HPV PCR); 3) had 6 or fewer lifetime sexual partners and 4) had normal PAP smears.

The mixture comprised, per 0.5 ml dose, 20 μg of HPV-16 L1 VLP, 20 μg of HPV-18 L1 VLP and was adjuvanted with 500 μg of aluminum hydroxide and 50 μg of 3D MPL. The placebo group was injected with 500 μg of aluminum hydroxide alone.

The HPV 16 VLPs are comprised of a 471 amino acid, C terminally truncated HPV L1 protein, with a deletion of 34 amino acids. The HPV 18 VLPs are comprised of a C terminally truncated 472 amino acid HPV L1 protein, with a deletion of 35 amino acids.

The vaccine efficacy (V.E.) against certain cancer HPV types was assessed, wherein the V.E. is the % improvement in protection against infection by the vaccine compared to a placebo group.

Cross protection was assessed by detecting the presence of nucleic acid specific for various oncogenic types in the vaccinees and control group. Detection was carried out using techniques as described in WO03014402, and references therein, particularly for non-specific amplification of HPV DNA and subsequent detection of DNA types using a LiPA system as described in WO 99/14377, and in Kleter et al, [Journal of Clinical Microbiology (1999), 37 (8): 2508-2517], the whole contents of which are herein specifically incorporated by reference.

Any suitable method can, however, be used for the detection of HPV DNA in a sample, such as type specific PCR using primers specific for each HPV type of interest. Suitable primers are known to the skilled person, or can be easily constructed given that the sequences of the oncogenic HPV types are known.

In detail, the methods section of the Lancet paper is reproduced here below, for completeness:

Harper et al, the Lancet. Nov. 13, 2004;364(9447):1757-65—Experimental Details.

The primary objective of this study was to assess vaccine efficacy in the prevention of infection with HPV-16, HPV-18, or both (HPV-16/18), between months 6 and 18 in participants who were initially shown to be seronegative for HPV-16/18 by ELISA and negative for HPV-16/18 DNA by PCR. Secondary objectives included: evaluation of vaccine efficacy in the prevention of persistent infection with HPV-16/18, and the evaluation of vaccine efficacy in the prevention of cytologically confirmed low-grade squamous intraepithelial lesions (LSIL), high-grade squamous intraepithelial lesions (HSIL), and histologically confirmed LSIL (CIN 1), HSIL (CIN 2 or 3) squamous cell cancer, or adenocarcinoma associated with HPV-16/18 infection between months 6 and 18, and months 6 and 27. The prevention of atypical squamous cells of undetermined significance (ASCUS) cytology associated with HPV-16/18 infection was added post-hoc to the outcome analyses.

We also did an exploratory analysis of the histopathological endpoints CIN 1 and 2 associated with HPV-16/18 DNA detected by PCR in lesional tissue. Other objectives included the assessment of vaccine immunogenicity, safety, and tolerability.

Investigators in North America (Canada and the USA) and Brazil recruited women for this efficacy study through advertisements or previous participation in an HPV cross-sectional epidemiology study that took place between July and December, 2000.

For each of the 32 study sites, an institutional review board approved the protocol, consent forms, and amendments. Women signed separate written consents for study participation and colposcopy. For those under 18 years, parental consent and assent from the participant were obligatory.

There were two study phases: an initial phase for vaccination and follow-up that concluded at month 18; and a blinded follow-up extension phase that concluded at month 27.

Women eligible for the initial phase (months 0-18) included healthy women aged 15-25 years, who had had no more than six sexual partners, no history of an abnormal Pap test or ablative or excisional treatment of the cervix, and no ongoing treatment for external condylomata; and who were cytologically negative, seronegative for HPV-16 and HPV-18 antibodies by ELISA, and HPV-DNA-negative by PCR for 14 high-risk HPV types (16, 18, 31, 33, 35, 39, 45, 51, 52, 56, 58, 59, 66, and 68) no more than 90 days before study entry.

Women who completed the initial phase of the study earliest, and who did not have ablative or excisional therapy of the cervix, or hysterectomy after enrolment, were eligible to participate in the extension phase of the study (months 18-27).

Procedures

Each dose of the bivalent HPV-16/18 virus-like particle vaccine (GlaxoSmithKline Biologicals, Rixensart, Belgium) contained 20 μg of HPV-16 L1 virus-like particle and 20 μg of HPV-18 L1 virus-like particle. Each type of virus-like particle was produced on *Spodoptera frugiperda* Sf-9 and *Trichoplusia ni* Hi-5 cell substrate with AS04 adjuvant containing 500 μg aluminum hydroxide and 50 μg 3-deacylated monophosphoryl lipid A (MPL, Corixa, Mont., USA) provided in a monodose vial. The placebo contained 500 μg of aluminum hydroxide per dose, and was identical in appearance to the HPV-16/18 vaccine. Every study participant received a 0.5 mL dose of vaccine or placebo at 0 months, 1 month, and 6 months.

Health-care providers obtained cervical specimens with a cervical brush and spatula (washed in PreservCyt, Cytyc Corporation, Boxborough, Mass., USA) for cytology and HPV DNA testing at screening and months 6, 12, and 18. At months 0 and 6, and subsequently every 3 months, women self-obtained cervicovaginal samples with two sequential swabs (placed in PreservCyt) for HPV DNA testing.[DM Harper, WW Noll, DR Belloni and BF. Cole, Randomized clinical trial of PCR-determined human papillomavirus detection methods: self-sampling versus clinician-directed—biologic concordance and women's preferences. *Am J Obstet Gynecol* 186 (2002), pp. 365-373] A central laboratory (Quest Diagnostics, Teterboro, N.J., USA) reported cytology results (ThinPrep, Cytyc Corporation) by use of the 1991 Bethesda classification system.

Protocol guidelines recommended colposcopy after two reports of ASCUS, or one report of atypical glandular cells of undetermined significance, LSIL or HSIL, squamous cell carcinoma, adenocarcinoma in situ, or adenocarcinoma. These guidelines also recommended biopsy for any suspected lesions.

The central histology laboratory made an initial diagnosis from the formalin-fixed tissue specimens for clinical management. A panel of three pathologists made a subsequent consensus diagnosis for HPV-16 and HPV-18 associated lesions with the CIN system. This consensus diagnosis also included review of the sections taken at the time of microdissection for PCR detection of lesional HPV DNA.

HPV DNA isolated from the cytology specimen (MagNaPure Total Nucleic Acid system, Roche Diagnostics, Almere, Netherlands) and from the cervical biopsy specimen (proteinase K extraction) was amplified from an aliquot of purified total DNA with the SPF10 broad-spectrum primers that amplify a 65 bp region of the L1 gene.[B Kleter, L J van Doorn, J ter Schegget et al., Novel short-fragment PCR assay for highly sensitive broad-spectrum detection of anogenital human papillomaviruses. *Am J Pathol* 153 (1998), pp. 1731-1739: L J van Doorn, W Quint, B Kleter et al., Genotyping of human papillomavirus in liquid cytology cervical specimens by the PGMY line blot assay and the SPF(10) line probe assay. *J Clin Microbiol* 40 (2002), pp. 979-983 and W G Quint, G Scholte, L J van Doorn, B Kleter, P H Smits and J. Lindeman, Comparative analysis of human papillomavirus infections in cervical scrapes and biopsy specimens by general SPF(10) PCR and HPV genotyping. *J Pathol* 194 (2001), pp. 51-58] The amplification products were detected by a DNA enzyme immunoassay. A line probe assay (LiPA Kit HPV INNO LiPA HPV genotyping assay, SPF-10 system version 1, Innogenetics, Gent, Belgium, manufactured by Labo Bio-medical Products, Rijswijk, Netherlands) detected 25 HPV genotypes (6, 11, 16, 18, 31, 33, 34, 35, 39, 40, 42, 43, 44, 45, 51, 52, 53, 56, 58, 59, 66, 68, 70, and 74). [B Kleter, L J van Doorn, L Schrauwen et al., Development and clinical evaluation of a highly sensitive PCR-reverse hybridization line probe assay for detection and identification of anogenital human papillomavirus. *J Clin Microbiol* 37 (1999), pp. 2508-2517] Any specimen that was positive by DNA enzyme immunoassay was tested by type-specific HPV-16 and HPV-18 PCR. HPV-16 type-specific PCR primers amplified a 92 bp segment of the E6/E7 gene and HPV-18 type-specific PCR primers amplified a 126 bp segment of the L1 gene. [M F Baay, W G Quint, J Koudstaal et al., Comprehensive study of several general and type-specific primer pairs for detection of human papillomavirus DNA by PCR in paraffin-embedded cervical carcinomas. *J Clin Microbiol* 34 (1996), pp. 745-747]

We defined incident cervical infection with HPV-16/18 as at least one positive PCR result for HPV-16 or HPV-18 during the trial, and persistent infection with HPV-16/18 as at least two positive HPV-DNA PCR assays for the same viral genotype separated by at least 6 months.[ H Richardson, G Kelsall, P Tellier et al., The natural history of type-specific human papillomavirus infections in female university students. *Cancer Epidemiol Biomarkers Prev* 12 (2003), pp. 485-490 and A B Moscicki, J H Ellenberg, S Farhat and J. Xu, Persistence of human papillomavirus infection in HIV-infected and -uninfected adolescent girls: risk factors and differences, by phylogenetic type. *J Infect Dis* 190 (2004), pp. 37-45] HPV-DNA test results were concealed from investigators during the study and cytological and histological diagnoses were only revealed for clinical management purposes. Analyses included HPV-16/18 DNA results for cervical specimens and combined cervical and self-obtained cervicovaginal specimens.

We collected serum from study participants at months 0, 1, 6, 7, 12, and 18 for assessment of immunogenicity. Serological testing for antibodies to HPV-16 and HPV-18 virus-like particles was by ELISA. Recombinant HPV-16 or HPV-18 virus-like particles were used as coating antigens for antibody detection (see webappendix http://image.thelancet.com/extras/04art10103webappendix.pdf). Seropositivity was defined as a titre greater than or equal to the assay cut-off titre established at 8 ELISA units/mL for HPV-16 and 7 ELISA units/mL for HPV-18. Typical natural titres were determined by use of blood samples obtained from women in the preceding epidemiology study who were found to be seropositive for HPV-16 or HPV-18 by ELISA.

Women recorded symptoms experienced during the first 7 days after vaccination on diary cards with a three-grade scale of symptom intensity. Additionally, they reported to study personnel by interview all adverse events within the first 30 days after vaccination. Information on serious adverse events and pregnancies was collected throughout the study.

Statistical Methods

Assuming a 6% cumulative incidence rate of both HPV-16 and HPV-18 type infections over 12 months, we estimated that 500 women per treatment group would provide 80% power to assess a lower limit of the 95% CI of the vaccine efficacy above zero. We assumed an 80% retention rate over 18 months. Interim analyses for efficacy, safety, and immunogenicity were done for future study planning purposes only; the O'Brien and Fleming method was used to adjust the uvalue for the final analysis after interim analyses occurred (overall $\alpha$=0.05; two-sided test).[PC O'Brien and TR. Fleming, A multiple testing procedure for clinical trials. *Biometrics* 35 (1979), pp. 549-556]

Stratified, block randomisation according to validated algorithms was centralised with an internet randomisation system. Stratification was according to age (15-17, 18-21, and 22-25 years) and region (North America and Brazil). Each vaccine dose was attributed a randomly chosen number based on specific participant information entered into the computerised randomisation system by study personnel. Treatment allocation remains concealed from investigators and the women participating in a long-term follow-up study.

The intention-to-treat and according-to-protocol cohorts are shown in the figure, in which the reasons for exclusion from analyses are listed in rank order; women who met more than one exclusion criterion were only counted once according to the highest ranking criterion. We refer to the sets of participants entered in the intention-to-treat and according-to-protocol analyses as cohorts, although the information used to restrict subject inclusion in the according-to-protocol was only known after follow-up.

We did both according-to-protocol and intention-to-treat analyses for efficacy. Calculation of vaccine efficacy in the according-to-protocol 18-month analysis was based on the proportion of participants with HPV-16/18 infection in the vaccinated versus placebo groups. Vaccine efficacy was defined as 1 minus the ratio between these two proportions; 95% CIs measured the precision of the efficacy estimates. p values were calculated with the two-sided Fisher's exact test. Corresponding rates were expressed as the numbers of cases with the outcome divided by the numbers of participants at risk. The according-to-protocol 18-month cohort included enrolled women who received three scheduled doses of vaccine and complied with the protocol as described in the figure.

Calculation of vaccine efficacy in the intention-to-treat and according-to-protocol 27-month analyses was based on the Cox proportional hazard model using the time-to-occurrence of cases with HPV-16/18 infection in the vaccinated versus placebo groups. This allowed controlling for the accrued person-time data in each group. Vaccine efficacy was calculated using 1 minus the hazard ratio and p values calculated using the log rank test. Corresponding rates were expressed as the number of cases divided by the total person-time. All enrolled women who received at least one dose of vaccine or placebo, were negative for high-risk HPV-DNA at month 0, and had any data available for outcome measurement were included in the intention-to-treat cohort. The according-to-protocol 27-month cohort included outcome results from the according-to-protocol 18-month cohort and results that occurred during the extension phase (from 18 months to 27 months).

Calculation of p values for the safety analysis was performed using Fisher's exact test comparisons. The cohort for safety analysis included all enrolled women who received at least one dose of vaccine or placebo and complied with specified, minimal protocol requirements (see figure below:).

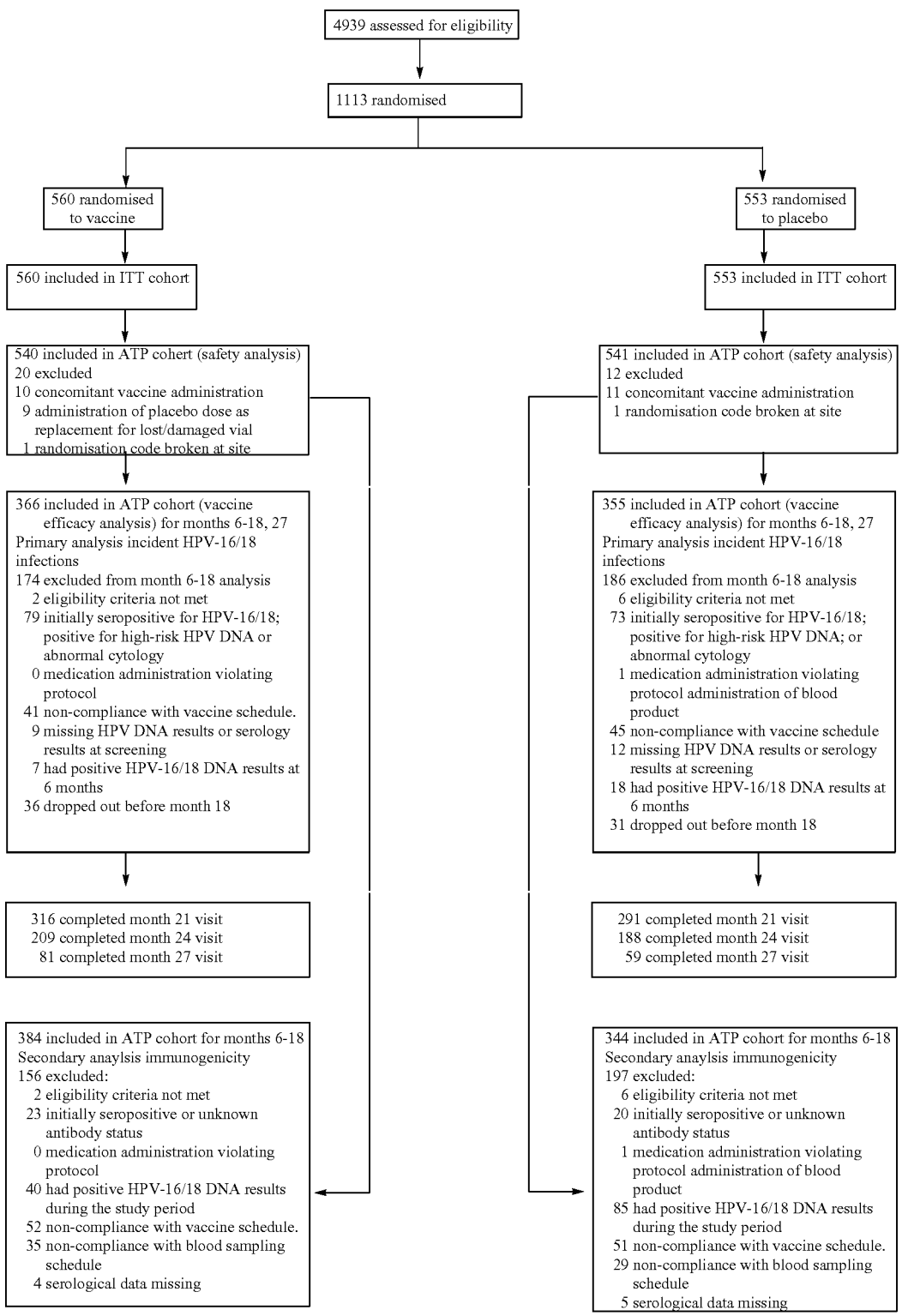

Immunogenicity was assessed in a subset of the according-to-protocol safety cohort, which included women with serology results at months 0, 7, and 18, who received all three doses of study vaccine or placebo according to schedule, complied with the blood sampling schedule, and did not become positive for HPV-16/18-DNA during the trial. Seropositivity rates between the vaccine and placebo groups were compared with Fisher's exact test (p<0·001 judged significant). Geometric mean titres were compared with ANOVA and Kruskal-Wallis test.

Block randomisation and statistical analyses were done with SAS version 8.2 (SAS Institute, Cary, N.C.).

Results

Results of the initial analysis on cross protection are presented in patent application WO2004/056389, the whole contents of which are herein incorporated by reference.

Further Analysis

An analysis was carried out on an "ATP" (According To Protocol) group for those patients who complied with all the criteria of the trial. In the ATP group all patients received 3 doses of vaccine at 0, 1 and 6 months and were seronegative at 6 months.

As demonstrated by the data presented in Table 4, immunization with a mixture of HPV16 and HPV18 VLPs provided statistically significant cross protection against incident infection by HPV types 31, 52 and 45 compared to the control.

Statistically significant cross protection against incident infection was also observed against the group of all HPV 16 related types (HPV-31, 33, 35, 52 and 58) and the group of all high risk types, excluding 16 and 18 (HPV 31, 33, 35, 39, 45, 51, 52, 56, 58, 59, 66, and 68).

Statistically significant cross protection against persistent infection was also observed against types 31 and 52 (see table 5), and was also observed against the group of all HPV 16 related types (see Table 5).

Statistically significant cross protection was also observed against cytological abnormalities associated with HPV 52, see table 6. Statistically significant protection was also observed against cytological abnormalities associated with the group of all HPV 16 related types (HPV-31, 33, 35, 52, and 58) and the group of all high risk types, excluding 16 and 18 (31, 33, 35, 39, 45, 51, 52, 56, 58, 59, 66, and 68).

TABLE 4

Efficacy against Incident Infections With 16/18 Related Types*

| | HPV type | Vaccine | | Control | | Vaccine Efficacy | |
|---|---|---|---|---|---|---|---|
| | | N | AR | N | AR | % | P Value |
| 16 related | HPV-31 | 1 | 0.2 | 10 | 2.4 | 90.0 | 0.006 |
| | HPV-33 | 6 | 1.4 | 6 | 1.4 | −0.2 | 1.000 |
| | HPV-35 | 1 | 0.2 | 3 | 0.7 | 66.5 | 0.624 |
| | HPV-52 | 6 | 1.4 | 16 | 3.9 | 63.0 | 0.031 |
| | HPV-58 | 5 | 1.2 | 5 | 1.2 | 0.0 | 1.000 |
| 18 related | HPV-45 | 0 | 0.0 | 5 | 1.2 | 100.0 | 0.031 |
| | HPV-59 | 4 | 0.9 | 2 | 0.5 | −100.5 | 0.448 |
| | All 16 related | 16 | 4.0 | 32 | 8.1 | 51.1 | 0.017 |
| | All 18 related | 4 | 1.0 | 7 | 1.7 | 43.0 | 0.384 |
| | All HR (except 16/18) | 32 | 9.0 | 53 | 15.6 | 42.3 | 0.011 |

*Cervical samples: ATP cohort

TABLE 5

Efficacy against Persistent Infections With 16/18 Related Types*

| | HPV type | Vaccine | | Control | | Vaccine Efficacy | |
|---|---|---|---|---|---|---|---|
| | | N | AR | N | AR | % | P Value |
| 16 related | HPV-31 | 2 | 0.48 | 9 | 2.15 | 78.5 | 0.030 |
| | HPV-33 | 3 | 0.71 | 5 | 1.18 | 40.2 | 0.476 |
| | HPV-35 | 1 | 0.24 | 1 | 0.24 | 0.4 | 0.998 |
| | HPV-52 | 5 | 1.20 | 21 | 5.10 | 77.1 | 0.001 |
| | HPV-58 | 4 | 0.95 | 6 | 1.42 | 34.1 | 0.515 |
| 18 related | HPV-45 | 1 | 0.24 | 4 | 0.94 | 75.4 | 0.174 |
| | HPV-59 | 3 | 0.71 | 0 | 0.00 | — | 0.083 |
| | All 16 related | 11 | 2.7 | 30 | 7.6 | 65.1 | 0.002 |
| | All 18 related | 4 | 1.0 | 4 | 1.0 | 1.0 | 0.989 |
| | All HR (except 16/18) | 36 | 10.1 | 46 | 13.5 | 27.1 | 0.155 |

*All samples; ATP cohort

TABLE 6

Efficacy against Cytological Abnormalities ass. With 16/18 Related Types*

| | HPV type | Vaccine | | Control | | Vaccine Efficacy | |
|---|---|---|---|---|---|---|---|
| | | N | AR | N | AR | % | P Value |
| 16 related | HPV-31 | 1 | 0.24 | 5 | 1.20 | 80.1 | 0.123 |
| | HPV-33 | 2 | 0.47 | 4 | 0.94 | 49.9 | 0.686 |
| | HPV-35 | 0 | 0.00 | 2 | 0.47 | 100 | 0.499 |
| | HPV-52 | 1 | 0.24 | 11 | 2.67 | 91 | 0.003 |
| | HPV-58 | 2 | 0.47 | 2 | 0.47 | 0.2 | 1.000 |
| 18 related | HPV-45 | 0 | 0.00 | 2 | 0.47 | 100 | 0.249 |
| | HPV-59 | 4 | 0.94 | 2 | 0.47 | −101 | 0.451 |
| | All 16 related | 5 | 1.2 | 18 | 4.6 | 72.8 | 0.005 |
| | All 18 related | 4 | 1.0 | 4 | 1.0 | 0.2 | 1.000 |
| | All HR (except 16/18) | 10 | 2.8 | 30 | 8.8 | 68.2 | <0.001 |

*ATP cohort

In tables 4, 5 and 6,

N=number of subjects in specific cohort

AR=Attack rate=n (number of subjects with HPV either incident infection, persistent infection or cytological abnormality, as appropriate for the table )/N % Vaccine efficacy is 1−(A/B)×100, adjusted for relative size of vaccine and placebo group, wherein A=% women in vaccine group with incident infection, persistent infection or cytological abnormality, as appropriate for the table

The invention claimed is:

1. An immunogenic composition comprising VLPs or capsomers from HPV 16, HPV 18, and at least one other HPV cancer type selected from the group consisting of HPV types 31 and 45, wherein the dose of the VLP or capsomer of the at least one other cancer type is reduced relative to that of HPV 16 or 18.

2. The composition according to claim 1 wherein the other cancer type is HPV 31.

3. The composition according to claim 1 wherein the other cancer type is HPV 45.

4. The composition according to claim 1 further comprising a VLP or capsomer of HPV 52.

5. The composition according to claim 1 wherein the other cancer types are HPV 31 and HPV 45.

6. The composition according to claim 1 wherein the other cancer types are HPV 31 and HPV 52.

7. The composition according to claim 1 wherein the other cancer types are HPV 52 and HPV 45.

8. The composition according to claim 1 wherein the other cancer types are HPV 31, HPV 45 and HPV 52.

9. The immunogenic composition according to claim 1 wherein the composition comprises at least 10 µg of HPV 16 VLPs or capsomers, at least 10 µg of HPV 18 VLPs or capsomers, and from 2 to 9 µg of VLPs or capsomers from the other cancer type.

10. The immunogenic composition according to claim 1 wherein the composition comprises at least 20 µg of HPV 16 VLPs or capsomers, at least 20 µg of HPV 18 VLPs or capsomeres, and from 5 to 15 µg of VLPs or capsomers from the other cancer type.

11. The immunogenic composition according to claim 10 wherein the composition comprises 10 µg of VLP or capsomer from the other cancer type.

12. The immunogenic composition according to claim 1 further comprising an adjuvant.

13. The composition according to claim 12 wherein the adjuvant is an aluminium salt.

14. The composition according to claim 13 wherein the adjuvant is aluminium hydroxide.

15. The composition according to claim 12 wherein the adjuvant is a lipid A derivative.

16. The composition according to claim 15 wherein the adjuvant is 3D MPL.

17. The composition according to claim 12 wherein the adjuvant is 3D MPL and aluminium hydroxide.

18. A vaccine comprising an immunogenic composition according claim 1 with a pharmaceutically acceptable excipient.

19. A method of preventing HPV infection or disease caused by HPV comprising administering to an individual in need thereof a composition according to claim 1.

20. A method for making the immunogenic composition of claim 1 comprising mixing VLPs or capsomers from HPV 16 and 18 with at least one other HPV cancer type, the other cancer type selected from the group consisting of HPV types 31 and 45, wherein the dose of the VLP or capsomer of the at least one other cancer types is reduced relative to that of HPV 16 or 18.

21. A method of prevention or treatment of HPV infection and/or disease comprising delivering to a individual an immunogenic composition comprising VLPs or capsomers from HPV 16 and 18 and at least one other HPV cancer type, the other cancer type selected from the group consisting of HPV types 31 and 45, wherein the dose of the VLP or capsomer of the at least one other cancer types is reduced relative to that of HPV 16 or 18.

* * * * *